United States Patent
Visser et al.

(10) Patent No.: US 10,081,819 B2
(45) Date of Patent: Sep. 25, 2018

(54) METHOD FOR MANUFACTURING A MIXED SOLUTION OF PROPIONATE AND ACETATE

(75) Inventors: Diana Visser, Rotterdam (NL); Arne Olav Sliekers, Breda (NL); Adriaan Dirk Kon, Meerkerk (NL)

(73) Assignee: Purac Biochem BV, Gorinchem (NL)

( * ) Notice: Subject to any disclaimer, the term of this patent is extended or adjusted under 35 U.S.C. 154(b) by 297 days.

(21) Appl. No.: 13/202,642

(22) PCT Filed: Feb. 22, 2010

(86) PCT No.: PCT/EP2010/052198
§ 371 (c)(1),
(2), (4) Date: Aug. 22, 2011

(87) PCT Pub. No.: WO2010/097362
PCT Pub. Date: Sep. 2, 2010

(65) Prior Publication Data
US 2011/0300257 A1    Dec. 8, 2011

Related U.S. Application Data

(60) Provisional application No. 61/202,400, filed on Feb. 25, 2009, provisional application No. 61/202,613, filed on Mar. 18, 2009.

(30) Foreign Application Priority Data

Feb. 25, 2009   (EP) ..................................... 09153615
Mar. 18, 2009   (EP) ..................................... 09155490

(51) Int. Cl.
| | | |
|---|---|---|
| A23L 1/315 | (2006.01) |
| A23L 1/226 | (2006.01) |
| A23L 1/318 | (2006.01) |
| A23L 2/56 | (2006.01) |
| C12P 7/52 | (2006.01) |
| C12P 7/54 | (2006.01) |

(52) U.S. Cl.
CPC .. *C12P 7/52* (2013.01); *C12P 7/54* (2013.01)

(58) Field of Classification Search
CPC .... C12P 39/00; C12P 7/52; C12P 7/54; C12P 7/56; C12N 1/20; A23L 1/226; A23L 2/56
USPC .............. 426/7, 650, 590, 644, 641
See application file for complete search history.

(56) References Cited

U.S. PATENT DOCUMENTS

| | | | | |
|---|---|---|---|---|
| 4,579,747 A | * | 4/1986 | Sugiyama et al. ............ | 426/548 |
| 4,676,987 A | | 6/1987 | Ahern | |
| 4,794,080 A | | 12/1988 | Mays | |
| 4,806,353 A | | 2/1989 | Thomas | |
| 4,814,273 A | | 3/1989 | Brumm | |
| 5,137,736 A | * | 8/1992 | Eaton ....................... | C12P 7/52 |
| | | | | 426/41 |

FOREIGN PATENT DOCUMENTS

| | | |
|---|---|---|
| EP | 141642 | 10/1984 |
| EP | 0563451 | 10/1993 |
| WO | WO 8504901 | 11/1985 |
| WO | WO 00/14052 | 3/2000 |

OTHER PUBLICATIONS

Frick, R. et al. 1999. Indirect methods of characterization of carbon dixide levels n fermentation broth. J. Bioscience Bioeng. 87: 344-351.*
JP-2005-060273. Enlish Abstract-pp. 17-18.*
Blinkova, E. V. et al. Russian J. Appl. Chem. 78: 1064-1066 (2005).*
European Search Report and Written Opinion of the European Patent Office Patent Office in counterpart foreign application No. PCT/EP2010/052198 filed Feb. 22, 2010.
State Intellectual Property Office of the People's Republic of China for Application No. 201080007325.2, dated Apr. 11, 2013.
New Zealand Intellectual Property Office, First Examination Report, dated Jan. 10, 3013, IP No. 605364.
Mexican Office Action dated Mar. 28, 2017 for corresponding Mexican Application No. MX/a/2012/011079.
Mexican Office Action dated Dec. 4, 2017 for corresponding Mexican Application No. MX/a/2012/011079.
Moon, N.J. (1983), Inhibition of the growth of acid tolerant yeasts by acetate, lactate and propionate and their synergistic mixtures, Journal of Applied Bateriology, 55: 453-460.

* cited by examiner

*Primary Examiner* — Hamid R Badr
(74) *Attorney, Agent, or Firm* — Peter J. Ims; Westman, Champlin & Koehler, P.A.

(57) ABSTRACT

A method for manufacturing a mixed solution comprising propionate and acetate includes adding acid to a fermentation product to obtain an acidified fermentation product comprising propionate and acetate with a pH in the range of 2.5 to 8. The method optionally includes removing carbonate-related compounds from the mixed solution.

16 Claims, No Drawings

METHOD FOR MANUFACTURING A MIXED SOLUTION OF PROPIONATE AND ACETATE

CROSS-REFERENCE TO RELATED APPLICATION

This Application is a Section 371 National Stage Application of International Application No. PCT/EP2010/052198, filed Feb. 22, 2010 and published as WO 2010/097362 A1 on Sep. 2, 2010, in English, which in turn is based on and claims benefits of U.S. Provisional Application No. 61/202,613, filed Mar. 18, 2009 and U.S. Provisional Application No. 61/202,400, filed Feb. 25, 2009.

BACKGROUND

The discussion below is merely provided for general background information and is not intended to be used as an aid in determining the scope of the claimed subject matter.

An aspect of the present invention pertains to a method for manufacturing a mixed solution of propionate, acetate, and optional other organic acid salts by upgrading the product of a fermentation process.

The use of fermentation processes for the manufacture of mixed solutions of propionate and acetate are known in the art.

However, the art does not describe the upgrading of the processing liquid. It has been found that there is need for a method for upgrading fermentation products, in particular fermentation products containing substantial amounts of carbonates or carbonate-related compounds. This is because the presence of carbonate-related compounds is undesired in various food and drink products.

The presence of carbonates in certain food and drink products is undesired in terms of quality and regulation. Further, the presence of carbonates may lead to problems such as precipitates or undesired gas or foam formation during use of the fermentation products containing these carbonates or the products, such as for example various food and drink products, in which these fermentation products containing the carbonates are used. The presence of carbonates may also lead to precipitation or gas or foam formation occurring during further processing of the liquid, in particular precipitation during a further concentration process. The precipitates formed will foul the equipment used for such concentration processes and create a very inefficient concentration process. The present invention pertains to such an upgrading process. Further problems solved by the present invention and associated advantages will become clear from the following description.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the present invention pertains to a method for manufacturing a mixed solution comprising propionate and acetate and for reducing the content of carbonate-related compounds herein.

The process according to the invention comprises:
providing a fermentation product comprising propionate, acetate, and carbonate-related compounds and
adding acid to the fermentation product to obtain an acidified fermentation product with a pH in the range of 2.5 to below 8 (hereinafter also referred to as the acidification step).

DETAILED DESCRIPTION

By the disclosed process, a solution is obtained which comprises propionate and acetate and which has a low total amount of carbonate-related compounds. The total amount of carbonate-related compounds is the sum of carbonates, bicarbonates and carbonic acid, or in other words $\Sigma(H_2CO_3, HCO_3^-, CO_3^{2-})$. This means that the total amount of carbonate-related compounds, expressed as mol/l in the final solution obtained via the process of the present invention is at most 0.05 mol/l at ambient temperature.

An advantage of this low total carbonate content is that further concentration steps can be carried out without precipitation of insoluble carbonate-related salts. A further advantage is that the low carbonate content reduces the risk of undesirable carbon dioxide (CO2) formation during use of the solution.

Without being bound to any theory, the hypothesis is that the addition of the acid results in the removal of carbonate-related compounds from the fermentation product in the form of a foam or gas comprising carbon dioxide. In a further aspect of the present invention, the method comprises an additional step for the removal of the carbonate-related compounds or for the removal of said foam or gas that is formed. This may be done by various means such as for example evaporation, by bubbling through the solution with other gases, by suction of the foam or gas that is formed, etceteras. It is also possible to simply keep the acidified fermentation product at rest for a certain amount of time until for example no further gas or foam formation is visually observed while optionally the product is being stirred.

In one embodiment the acidification step is combined with a process step in which the temperature of the product is increased. This may be done simultaneously or subsequently (i.e. the temperature is increased during the acidification step, the temperature of the fermentation product is first increased or the temperature of the resulting acidified fermentation product is increased). This will favor the removal of the carbonate-related compounds in the form of said carbon dioxide-comprising gas or foam.

The amount of propionate in the fermentation product that is used as starting material in the process according to the invention is generally in the range of 0.5-10 wt % (weight-based percentage), more in particular in the range of 1-5 wt %.

The amount of acetate in the fermentation product is generally in the range of 0.1-5 wt %, more in particular in the range of 0.5-2 wt %.

The direct pH of the fermentation product that is used as starting material is generally in the range of 6-9, more in particular in the range of 6.5 to 8.5.

The way in which the fermentation product used as starting material in the present invention is obtained is not critical to the process.

In one embodiment the fermentation product that is used as starting material may be obtained by subjecting a lactic acid-containing medium to a fermentation process using bacteria.

Suitable bacteria include bacteria from the family of the genus Propionibacteriaceae, such as *Propionibacterium acidi-propionici*, *Propionibacterium freudenreichii*, *Propionibacterium thoeni* and/or *Propionibacterium jensenii*, or from the genus *Selenomonas* (e.g. *Selenomonas rumantium*). The use of *Propionibacterium freudenreichii* subsp. *shermanii* may be preferred.

The fermentation process is generally carried out at a temperature in the range of 10-70° C., in particular in the range of 25-55° C., more in particular in the range of 25-35° C. Suitable fermentation processes are known in the art including U.S. Pat. No. 4,676,987, U.S. Pat. No. 4,814,273, EP 0563451, EP 141642, WO 85/04901 and U.S. Pat. No. 4,794,080 and require no further elucidation here. The resulting fermentation product may be used as the starting material in the process described herein.

The fermentation product is, after completion of the fermentation, in one embodiment further purified by removal of biomass including bacteria and various impurities. If the biomass is removed, it may be partially or completely be removed from the medium. Any method known to the skilled person for this (partial) biomass removal processing step may be used, e.g. and not limited to ultrafiltration, microfiltration, static decantation, or centrifugation.

The fermentation product obtained after said (partial) removal of the biomass can be used as starting material in the process described herein.

In the acidification step of the process, an acid is added to the fermentation product to obtain a pH in the range of 2.5 to below 8. In particular, the pH is in the range of 3 to 7, and more particular in the range of 3 to about 6.6 or 6.8. One fermentation product is acidified to obtain an acidified fermentation product with a pH in the range of 3 to 7 as then the majority of the carbonate-related compounds is removed and using said fermentation product will in most of the food and drink applications cause no further problems in terms of e.g. precipitates or gas/foam formation. Most ideal is the acidification of the fermentation product until a pH below 6.8 as the amount of carbonate-related compounds is even further reduced.

The amount of acid that is added depends on the pH of the fermentation product and/or on the way in which the fermentation product is further processed or applied, such as e.g. in certain food or drink products. The end concentration of added acid is generally in the range of 0.1-60 wt % of the fermentation product, more in particular in the range of 10-50 wt % and most preferably in the range of 25-50 wt %.

It is noted that the pH value is the parameter that determines the effect of the process. The values mentioned above for the amount of acid are given for guidance.

The acidified product obtained generally comprises propionate in an amount of the range of 0.5-10% wt %, more in particular in the range of 1-7% wt %, acetate in an amount of 0.1-7% wt %, more in particular in the range of 0.5-2.5% wt %, and added acid in the end concentrations as mentioned earlier. It is noted that if the added acid comprises propionic and/or acetic acid, the ranges for these components are to be calculated by combining the ranges given above for the respective acids with the range given for the added acid.

The acid may be selected from organic or inorganic acids. Suitable inorganic acids include inorganic acids selected from hydrochloric acid, and nitrogen-, sulphur-, and phosphorus-containing acids. Within this group hydrochloric acid or phosphorus-containing acid is preferred.

Suitable organic acids include acids selected from carboxylic acids with 1-10 carbon atoms, which are optionally substituted with hydroxy groups. Suitable acids include citric acid, malic acid, lactic acid, gluconic acid, acetic acid (may also be in the form of vinegar), succinic acid, propionic acid, tartaric acid, fumaric acid, ascorbic acid, sorbic acid and benzoic acid.

Within the group of organic acids the use of lactic acid, acetic acid, citric acid and mixtures thereof is preferred due to amongst others their antimicrobial properties. Ascorbic is also preferred because of its anti-oxidative properties.

The addition of the acid results in the removal of carbonate-related compounds from the fermentation product in the form of carbon dioxide. The amount of carbonate-related compounds removed from the system is generally in the range of between 1-30 gram $CO_2$ (i.e. total amount of carbonate-related compounds expressed as $CO_2$) per liter fermentation medium, in particular 5-15 gram $CO_2$ per liter fermentation medium.

The amount of acid added is generally sufficient to remove at least 60% of the carbonate-related compounds present in the fermentation product in the form of carbon dioxide, more in particular at least 75%, even more in particular at least 90%. It was found that even more than 95% could be removed via the process according to the present invention.

In a further embodiment of the process, the fermentation product (partially or completely free from biomass or not at all) may be concentrated before the acid is added or the acid is added during concentration. The fermentation product cannot be concentrated too far in order to avoid precipitates fouling up the equipment and reducing the efficiency of the concentration process but it is possible to concentrate up to a product having a propionate concentration of about 20 wt %, more preferably up to 25 or even 30 wt %. To obtain a product having a higher propionate concentration than the latter, either an additional acidification step is required and/or a further raise in temperature.

Dependent on the pH of the fermentation product obtained after addition of the acid to the fermentation product (which may be concentrated or not) a next step of the process may comprise the addition of a base to the resulting acidified fermentation product comprising propionate and acetate in order to obtain a product with a direct pH of at least 5 (hereinafter also referred to as the base-addition step or the neutralization step). This is of course only necessary in the case that an acidified fermentation product is obtained with a pH below this value.

More in particular, the pH after addition of said base may be at least 6 and preferably at least 6.5. While the upper limit for the pH is not critical, the pH will generally be at most 8 and more in particular at most 7.5. At a pH of between 5 and 8, a product is obtained that can be efficiently further processed in for example a concentration step or is suited for direct application in e.g. food and drink products. For example, meat products, including fish and poultry products, have a more neutral pH and accordingly a product having a pH of about 7 to 7.5 and up to maximally 8 will be more suitable for this type of food products while the fermentation product of the present invention may have a lower pH of about 5 to 6 if it is going to be used in a more general (non-meat) food or drink product.

If a fermentation product (concentrated or not) is obtained having a pH, after acidification, of above 5 or above the preferred values as described above, no addition of any base is necessary and the fermentation product may be further processed, e.g. concentrated, and/or directly applied in e.g. a food or drink product and in particular in a meat-based food product.

The nature of the base used in this step is not critical for the process according to the invention. Suitable bases include NaOH, KOH, NH3, Ca(OH)2, Mg(OH)2, and NH3OH. The use of a food-compatible base may be preferred if the final product is to be used in a food application. The use of KOH or NaOH may be particularly preferred, as these compounds are inexpensive, easily accessible, and food compatible.

The amount of base that is added depends on the pH of the fermentation product. As mentioned earlier with regards to the added acid, it is noted that the pH value is the parameter that determines the effect of the process.

The product of the base addition step thus has a pH of at least 5, more in particular at least 6, even more in particular at least 6.5. The pH is generally most 8 and more in particular at most 7.5. When not concentrated in a earlier step, the product of the base addition step generally comprises propionate in an amount of the range of 0.5-10% wt %, more in particular in the range of 1-7% wt %, acetate in an amount of 0.1-7% wt %, more in particular in the range of 0.5-3% wt %, and added acid in an amount of 0 to 60 wt %, in particular in an amount of 10 to 50 wt % and more particularly in an amount of 25 to 50 wt %. As mentioned earlier, it is again noted that the added acid may preferably comprise citric acid, acetic acid, lactic or a combination thereof but may also comprise propionic acid optionally in combination with one or more of the above-mentioned other acids. In the case that the added acid comprises propionic and/or acetic acid, the ranges for these components are to be calculated by combining the ranges given above for the respective acids with the range given for the added acid.

It has appeared that when the fermentation product has not been concentrated prior to the acidification step, the concentration of the various organic acids salts in the fermentation liquid is generally rather low. There is therefore a need for a method allowing the manufacture of more concentrated solutions of the salts or these organic acids, in particular, a more concentrated solution comprising propionate and acetate than the solutions obtainable by methods known in the art.

In one embodiment, the fermentation product after acidification and/or the fermentation product after the base addition step is subjected to a concentration step to obtain a more concentrated product comprising propionate and acetate. The concentration step may be carried out by any method known in the art for the purpose. Suitable methods include for example evaporation, reversed osmosis, and spray drying and/or combinations hereof. The concentration step can be carried out to form a solution, but it is also possible to form a dried product via for example extrusion or spray-drying. The fact that the carbonate concentration in the solution has been reduced ensures that the formation of a precipitate can be prevented. The reduced carbonate concentration also reduces the risk of carbonate causing problems in further processing steps.

In an embodiment the acid used for acidification is lactic acid. In that case, the non-concentrated fermentation product obtained after the addition of acid and a base, generally comprises lactate in an amount of 30-50 wt %, propionate in an amount of 0.5-7 wt %, and acetate in an amount of 0.5-7 wt %. This product can be concentrated to form an aqueous solution which may comprise lactate in an amount of 60-95 wt %, propionate in an amount of 1-14 wt %, and acetate in an amount of 1-14 wt %. This product has been found to be attractive in various commercial applications, including as antimicrobial agent in food and drink applications and as taste enhancer. It was further found to be particularly suited for application in uncured meat and poultry products as the product displayed a particular taste profile having a positive contribution to the sensory properties of the uncured meat and poultry products.

The process described herein provides a method to prevent gas or foam formation during use of the propionate and acetate-comprising fermentation product in further processing or application in for example food and drink products due to the removal of carbonates or carbonate-related compounds in an earlier stage. The process described herein further prevents precipitation of carbonates or carbonate-related compounds after concentration. It is suitable for the removal of carbonate-related compounds in the form of carbon dioxide before concentration in all fermented food ingredients, e.g., fermentation products of natural food ingredients containing anaerobic fermentation products such as propionate, acetate, ethanol, or a combination of these. Also carbonate-related compounds and carbonates can be removed in this way from natural ferments containing any product from aerobic fermentation.

Aspects of the present invention are further illustrated by the following non-limitative examples.

EXPERIMENTS

Experiment 1: Without Addition of Acid

A fermentation broth was produced containing propionate and acetate. Biomass was removed by means of ultrafiltration. The clear ultrafiltration permeate was concentrated 10 times during evaporation at 85 mbar and 60 degrees Celsius to a concentration of about 20 wt % propionate. Solids precipitated immediately to the bottom and the pH increased from about 7 to about 10.5 due to the release of carbon dioxide gas.

Experiment 2: With Addition of Acid

The fermentation broth produced in experiment 1 was now first acidified by addition of lactic acid to a pH of about 3 to 3.5. The lower pH resulted in foaming carbon dioxide gas. After the foaming stopped, the pH of the acidified fermentation broth was brought back to a pH of about 6.5 to 7 by means of addition of potassium hydroxide. The resulting fermentation product was concentrated a factor three. No precipitation nor any gas formation occurred.

Afterwards, the pH was set to 5.7 by addition of a lactic acid/sodium hydroxide buffer and the product was stored for 6 months. No solids precipitated during these 6 months.

Experiment 3: Different Base

Experiment 2 was repeated but in stead of potassium hydroxide as base sodium hydroxide was added. No precipitation nor any gas formation occurred during evaporation or during storage afterwards.

Experiment 4

A medium containing 45 g/l sodium lactate was fermented to a fermentation product comprising propionic acid (2.3% (w/w)) and acetic acid (0.9% (w/w)). Temperature was maintained at 30° C. pH was controlled at 6.5 by addition of NaOH (10% (w/v)). First the fermentation product was subjected to a heating step and the temperature was increased to 75° C. With a carbon dioxide flow meter a clear increase of carbon dioxide removal from the fermentation product was observed at this higher temperature. Decreasing the pH to 5.5 by addition of lactic acid resulted in a higher flow of carbon dioxide removed. Finally this fermentation product was concentrated by a factor 7. No precipitated or floating carbonate particles were visible in the fermentation product or in the final concentrated fermentation product.

The invention claimed is:

1. A method for manufacturing a mixed solution comprising propionate and acetate, the method comprising:
providing a fermentation product having a pH of from 6 to 9 and comprising propionate, acetate, and carbonate-related compounds wherein said fermentation product is provided by subjecting lactate and/or carbohydrates in an aqueous medium to a fermentation step using bacteria followed by at least partial removal of the bacteria;
after the at least partial removal of the bacteria, adding an acid selected from lactic acid, acetic acid, citric acid or mixtures thereof to the fermentation product to obtain an acidified fermentation product comprising propionate and acetate with a pH in the range of 2.5 to 5 and containing at most 0.05 mol/l of carbonate-related compounds at ambient temperature, and
adding a base to the acidified fermentation product to obtain a neutralized fermentation product with a pH of at least 5, such that the formation of unwanted precipitates, foams or gases in the fermentation product is minimized.

2. The method according to claim 1 wherein the method comprises a step of removing carbonate-related compounds.

3. The method according to claim 1 wherein a base is added to the acidified fermentation product to obtain a neutralized fermentation product with a pH of from 6 to 8.

4. The method according to claim 1, wherein the fermentation product is subjected to a heating step prior to or simultaneously with addition of the acid and/or prior to or simultaneously with addition of the base and/or after addition of said base.

5. The method according to claim 1, wherein the fermentation product is subjected to a concentration step prior to adding the acid and/or prior to adding the base and/or after adding the base.

6. The method according to claim 1 wherein the fermentation product comprising propionate, acetate, and carbonate-related compounds, is provided by subjecting lactate and/or carbohydrates in an aqueous medium to a fermentation step using bacteria, followed by complete removal of the bacteria.

7. The method according to claim 1, wherein a base is added to the acidified fermentation product to obtain a neutralized fermentation product with a pH of between 6 and 7.5.

8. The method according to claim 1, wherein the added acid comprises lactic acid.

9. The method according to claim 5, wherein the concentration step is applied after adding said base and a solution comprising lactate in an amount of 30-50 wt %, propionate in an amount of 0.5-7 wt %, and acetate in an amount of 0.5-7 wt % is concentrated to form a solution comprising lactate in an amount of 60-95 wt %, propionate in an amount of 1-14 wt %, and acetate in an amount of 1-14 wt %.

10. An aqueous solution obtained by the process defined in claim 1, said solution comprising lactate in an amount of 30-50 wt %, propionate in an amount of 0.5-7 wt %, and acetate in an amount of 0.5-7 wt %, said aqueous solution having a total amount of carbonate-related compounds of at most 0.05 mol/l at ambient temperature.

11. An aqueous solution obtained by the process defined in claim 1, said solution comprising lactate in an amount of 60-95 wt %, propionate in an amount of 1-14 wt %, and acetate in an amount of 1-14 wt %, said aqueous solution having a total amount of carbonate-related compounds of at most 0.05 mol/l at ambient temperature.

12. A method for manufacturing food, meat or drink products comprising adding thereto the aqueous solution of claim 10 as an additive or as a taste enhancer in the food, meat or drink products.

13. A method of manufacturing a meat product comprising adding thereto the aqueous solution of claim 10 as a taste enhancer in meat products selected from uncured meat and poultry products.

14. A method for manufacturing food, meat or drink products comprising adding thereto the aqueous solution of claim 11 as an additive or as a taste enhancer in the food, meat or drink products.

15. A method of manufacturing a meat product comprising adding thereto the aqueous solution of claim 11 as a taste enhancer in meat products selected from uncured meat and poultry products.

16. The method according to claim 1, wherein the provided fermentation product has a pH of from 6.5 to 8.5.

* * * * *